United States Patent
Schlama et al.

(12) 
(10) Patent No.: US 6,855,842 B1
(45) Date of Patent: Feb. 15, 2005

(54) INTERMEDIATES FOR MAKING A BEZOFURAN OR BENZOTHIOPHENE DERIVATIVE NITRATED IN POSITION 5 AND USES THEREOF

(75) Inventors: Thierry Schlama, Dardilly (FR); Armand Mettling, Mulhouse (FR); Philippe Karrer, Zillisheim (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/110,441

(22) PCT Filed: Oct. 23, 2000

(86) PCT No.: PCT/FR00/02937

§ 371 (c)(1),
(2), (4) Date: Apr. 11, 2002

(87) PCT Pub. No.: WO01/28974

PCT Pub. Date: Apr. 26, 2001

(30) Foreign Application Priority Data

Oct. 21, 1999 (FR) ............................................. 99 13250

(51) Int. Cl.$^7$ ................................................ C07C 69/76
(52) U.S. Cl. ............................... 560/8; 560/9; 560/13; 560/20; 562/400; 562/433; 562/434
(58) Field of Search ........................... 560/8, 9, 13, 20, 560/17; 562/400, 433, 434

(56) References Cited

FOREIGN PATENT DOCUMENTS

| DE | 30 31 738 | 4/1982 | ......... C07D/333/54 |
|---|---|---|---|
| EP | 0 129 034 | 12/1984 | ......... C07C/69/712 |
| WO | 97/24122 | 7/1997 | ......... A61K/31/44 |

OTHER PUBLICATIONS

Jacobs et al, JACS, vol. 39, pp. 2188–2224, 1917.*
March, Advanced Organic Chemistry, Fourth Edition, pp. 522 to 524, 1992.*
Jacobs et al, JACS, vol. 39, pp. 2188–2224.*
Patel, Vinod F. et al: J. Org. Chem. (1997) 62(25), 8868–8874, XP002142466.
Bordin, Franco et al.: Gazz. Chim. Ital. (1969), 99(11), 1177–92, XP002142467.
Chemical Astracts, vol. 116, No. 5, Feb. 3, 1992, abstract No. 41094, Kwiecien, Halina et al.; XP002142471.
Edwards, Colin R. et al;, J. Heterocycl. Chem (1987), 24(2), 495–6, XP002142470.
Suzuki, Tsuneo et al.; Bull.Chem.Soc. Jpn. (1983), 56(9), 2762–7, XP002142469.
Jacobs, Walter A et al: Journal of the American Chemical Society., vol. 39, No. 8, pp. 2188–2224. XP000924885 Amer. Chem. Society, Washington.
Hullar, Theodore L. et al.: J. Med. Chem. (1969), 12(3), 420–4, XP002142468.
K. Fries et al: Justus Liebigs Annalen Der Chemie, XX, XX, vol. 527, No. 527, 1937, pp. 83–114–110, XP002087887.
XP002142473—JP 56 059718 A (Ihara Chem Ind Co Ltd), May 23, 1981.
Chemical Abstracts, vol. 99, No. 9, Aug. 29, 1983, abstract No. 70551, Fodor, Tamas et al: XP002142472.
International Search Report.

* cited by examiner

*Primary Examiner*—Rita Desai
*Assistant Examiner*—Hector M. Reyes

(57) ABSTRACT

The invention concerns novel nitroaromatic compounds of general formula (I') wherein: R, R'1, R2, Z and n are as defined in claim 1. The invention also concerns a method for preparing nitroaromatic compounds nitrated in position 4. The invention further concerns the use of said compounds for preparing heterocyclic benzofuran or benzothiophene derivatives nitrated in position 5. The invention concerns particularly the preparation of 2-alkyl-5-nitrobezofuran.

24 Claims, No Drawings

INTERMEDIATES FOR MAKING A BEZOFURAN OR BENZOTHIOPHENE DERIVATIVE NITRATED IN POSITION 5 AND USES THEREOF

This application is an application under 35 U.S.C. Section 371 of International Application No. PCT/FR00/02937 filed on Oct. 23, 2000.

The present invention relates to novel nitroaromatic compounds and to a process for their preparation.

The invention also relates to the use of these compounds in preparing heterocyclic benzofuran or benzothiophene type derivatives nitrated in the 5-position.

More particularly, the invention relates to the preparation of a 2-alkyl-5-nitrobezofuran.

Benzofuran or benzothiophene type structures are encountered in many molecules used in the pharmaceutical field. In particular, European patent EP-A-0 471 609 describes a process for preparing n-butyl-2-nitro-5-benzofuran, which consists of reacting 2-hydroxy-5-nitro-benzyltriphenylphosphonium bromide with pentanoyl chloride, in the presence of pyridine: 2-hydroxy-5-nitro-benzyltriphenylphosphonium bromide is obtained from 2-hydroxy-5-nitro-benzyl bromide and triphenylphosphine.

A completely different synthesis route involving different intermediates has now been discovered.

The present invention provides novel nitroaromatic compounds with general formula:

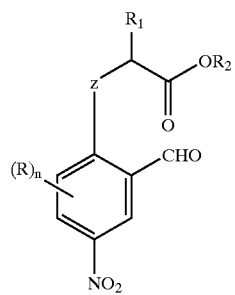

(I')

in which:
- $R'_1$ represents a linear or branched alkyl group containing 1 to 12 carbon atoms, a phenyl group that may be substituted by an alkyl group containing 1 to 4 carbon atoms, or a halogenophenyl group;
- $R_2$ represents a hydrogen atom, a hydrocarbon group containing 1 to 12 carbon atoms, which may be a linear or branched alkyl group, a cycloalkyl group, a phenyl group or a phenylalkyl group;
- Z represents an oxygen or sulphur atom;
- R represents a hydrogen atom or a substituent;
- n is a number equal to 0.1, 2 or 3, preferably 0;
- when n is greater than 1, two groups R and the successive 2 atoms of the benzene ring can together form a saturated, unsaturated or aromatic cycle containing 5 to 7 carbon atoms;

In formula (I'), the benzene ring can carry a substituent.

The scope of the invention does not exclude the presence on the benzene ring of any type of substituent, provided that it does not react under the conditions of the invention.

More particular examples of group R that can be mentioned include:
- a hydroxyl group;
- a linear or branched alkyl group containing 1 to 6 carbon atoms, preferably 1 to 4 carbon atoms, such as methyl, ethyl, propyl, isopropyl, butyl, isobutyl, sec-butyl, tert-butyl;
- an alkoxy group containing 1 to 6 carbon atoms, preferably 1 to 4 carbon atoms;
- an ester group containing 1 to 10 carbon atoms, preferably 1 to 4 carbon atoms;
- an alkylamide group containing 1 to 6 carbon atoms, preferably 1 to 4 carbon atoms;
- a carboxamide group;
- a halogen atom;
- a trifluoromethyl group.

Preferred compounds of the invention have formula (I') in which R represents a hydrogen atom, a methyl or ethyl group, or a methoxy or ethoxy group.

When n is greater than 1, two groups R and the successive 2 atoms of the benzene ring can together form a saturated, unsaturated or aromatic cycle containing 5 to 7 carbon atoms, preferably 6 carbon atoms. Advantageously, two groups R form a benzene ring.

Group $R'_1$, is advantageously an alkyl group containing 1 to 4 carbon atoms.

The invention does not exclude the fact that $R_2$ represents a further group such as cycloalkyl, phenyl or arylalkyl, but since group $R_2$ is eliminated, it is important from an economic viewpoint that it should be as simple as possible, for example a lower alkyl group, i.e., containing 1 to 4 carbon atoms. $R_2$ can also represent a hydrogen atom, which corresponds to the presence of a carboxylic group.

In formula (I'), Z preferably represents an oxygen atom.

In a further aspect, the present invention provides a process for preparing nitroaromatic compounds with formula (I):

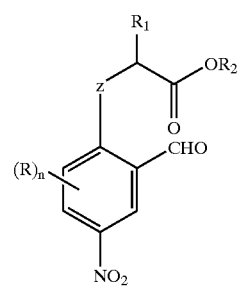

(I)

in which:
- $R_1$ represents a hydrogen atom, a linear or branched alkyl group containing 1 to 12 carbon atoms, a phenyl group that may be substituted by an alkyl group containing 1 to 4 carbon atoms, or a halogenophenyl group;
- $R_2$ represents a hydrogen atom, a hydrocarbon group containing 1 to 12 carbon atoms, which may be a linear or branched alkyl group, a cycloalkyl group, a phenyl group or a phenylalkyl group;
- Z represents an oxygen or sulphur atom;
- R represents a hydrogen atom or a substituent;
- n is a number equal to 0.1, 2 or 3, preferably 0;
- when n is greater than 1, two groups R and the successive 2 atoms of the benzene ring can together form a saturated, unsaturated or aromatic cycle containing 5 to 7 carbon atoms;

characterized in that it consists of carrying out selective nitration in the 4 position, using a source of $NO_2^+$ and in the presence of sulphuric acid, of an aromatic compound with formula (II):

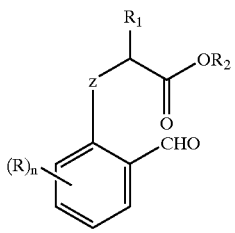

(II)

in which formula (II), R, $R_1$, $R_2$, Z and n have the meanings given above.

The invention also encompasses nitration of a compound with formula (II) in its acid form or in its ester form, i.e., a compound with formula (II) in which $R_2$ is either a hydrogen atom or a hydrocarbon group.

In a further aspect, the invention provides a process for preparing a compound with formula (II), consisting of reacting:

a compound of the 2-hydroxy- or 2-thiobenzaldehyde type with formula (III):

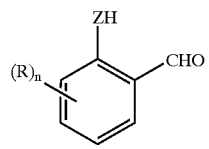

(III)

in which formula (III), R, Z and n have the meanings given above;

and a carboxylic acid or a derivative with formula (IV) comprising a leaving group:

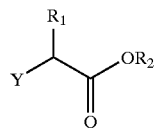

(IV)

in which formula (IV):

Y represents a leaving group, preferably a halogen atom or a sulphonic ester group with formula —$OSO_2$—R where R is a hydrocarbon group;

$R_1$, $R_2$ have the meanings given above.

In the formula for the sulphonic ester group, R is a hydrocarbon group of any nature. However, given that Y is a leaving group, it is important from an economic viewpoint that R should be simple in nature, and more particularly represents a linear or branched alkyl group containing 1 to 4 carbon atoms, preferably a methyl or ethyl group; however, it can also represent a phenyl or tolyl group or a trifluoromethyl group, for example. Preferably, group Y is a triflate group, corresponding to a group R representing a trifluoromethyl group.

Preferred leaving groups that can be selected are halogen atoms, namely bromine, chlorine or iodine, preferably a bromine or chlorine atom.

The invention also encompasses the use of a compound with formula (I) for the preparation of a heterocyclic compound with general formula (V):

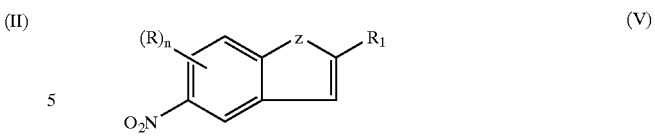

(V)

in which formula (V), R, $R_1$, Z and n have the meanings given above, optionally by saponification when $R_2$ is an ester function, followed by cyclising.

In accordance with the process of the invention, novel intermediates with formula (I') are prepared.

They are obtained by a selective nitration reaction in the 4 position of compounds with formula (II) in which $R_1$ is a linear or branched alkyl group containing 1 to 12 carbon atoms, a phenyl group that may be substituted by an alkyl group containing 1 to 4 carbon atoms, or a halogenophenyl group.

It has been discovered that it is only possible to carry out selective nitration in a position para to the O or S atom if the starting substrate is an O- or S-alkylated phenolic or thiophenolic substrate.

It has been discovered that nitration is not selective if the starting substrate is a phenolic substrate containing free OH or SH groups.

It has also been discovered that nitration is only carried out under good conditions if the $NO_2^+$ source is combined with sulphuric acid.

The selective nitration process of the invention is applicable both to preparing novel compounds with formula (I') in which $R'_1$, represents a linear or branched alkyl group containing 1 to 12 carbon atoms; a phenyl group that may be substituted by an alkyl group containing 1 to 4 carbon atoms or a halogenophenyl group, and to compounds with formula (I) in which $R_1$ has the same meaning as $R'_1$ but also includes representing a hydrogen atom.

Compounds with formula (I) or (I') can be obtained by nitration of an O- or S-alkylated compound with formula (II), by reacting the latter with a source of $NO_2^+$: preferably, the reaction may or may not be carried out in an organic solvent.

To this end, said compound is reacted with a source of $NO_2^+$.

It is possible to start with nitrogen dioxide $NO_2$, nitrous anhydride $N_2O_3$, dinitrogen tetroxide $N_2O_4$, or nitric oxide NO associated with an oxidising agent such as nitric acid, nitrogen dioxide or oxygen. When the reactant is gaseous under the reaction conditions, it is bubbled into the medium.

It is also possible to use nitrous acid, a nitrose or nitrosyl sulphate or a nitrous salt, preferably an alkali metal salt, still more preferably sodium associated with an oxidising agent, preferably nitric acid.

It is also possible to use alkyl nitrites associated with an oxidising agent, more particularly those with formula (VII):

$R_a$—ONO     (VII)

in which formula (VII), $R_a$ represents a linear or branched alkyl group containing 1 to 12 carbon atoms, preferably 1 to 4 carbon atoms.

The quantity of $NO_2^+$ source is at least equal to the stoichiometric quantity of the O- or S-alkylated aromatic compound. The ratio between the number of moles of $NO_2^+$ source and the number of moles of aromatic O- or S-alkylated compound is advantageously in the range 1.0 to 1.2.

Preferably, a concentrated nitric acid solution is used with a preferred concentration in the range 70% to 99%.

As mentioned above, the NO$_2^+$ source is associated with sulphuric acid.

In a variation, the process of the invention consists of using a nitrating mixture (mixture of nitric acid and sulphuric acid comprising 50% to 98% by weight of nitric acid).

The quantity of nitric acid, expressed as the mole ratio of the O- or S-alkylated aromatic compound/nitric acid, is generally in the range 0.9 to 1.1, preferably in the range 0.95 to 1.05.

The quantity of sulphuric acid, expressed as the mole ratio of the O- or S-alkylated aromatic compound/sulphuric acid, is generally in the range 0.9 to 1.1, preferably in the range 0.95 to 1.05.

The concentration of sulphuric acid is advantageously in the range 50% to 98%.

To this end, nitric acid or a precursor of nitric acid is used, such as dinitrogen tetroxide.

The nitration reaction can optionally be carried out in an organic solvent that is inert under the reaction conditions.

More particular examples of organic solvents that can be cited are aliphatic halogenated hydrocarbons, more particularly perchlorinated hydrocarbons such as tetrachloromethane, hexachloroethane; partially chlorinated hydrocarbons such as dichloromethane, and 1,2-dichloromethane.

Dichloromethane is the preferred solvent.

Regarding the concentration of the O- or S-alkylated aromatic compound in the reaction medium, it is preferably in the range 0.2 to 3 mole/l, more preferably in the range 0.3 to 1.5 mole/l.

This is generally introduced in the liquid form.

The reaction is advantageously carried out at a temperature in the range −10° C. to 20° C., preferably in the range −5° C. to 10° C., and in an inert gas atmosphere.

The process of the invention is generally carried out at atmospheric pressure.

In a preferred variation of the process of the invention, the nitration step is carried out in a controlled inert gas atmosphere. A rare gas atmosphere can be established, preferably argon, but it is cheaper to use nitrogen.

A number of implementations can be envisaged.

In a first variation, the sulphuric acid solution is charged first, followed by the O- or S-alkylated aromatic compound and the nitric acid at the same time.

In a further variation, the sulphuric acid and nitric acid solution is introduced then the O- or S-alkylated aromatic compound is added, preferably in portions, or it is poured in continuously.

In a still further variation, the O- or S-alkylated aromatic compound is introduced into a base stock on the one hand and the sulphuric and nitric acid on the other hand.

The reaction advantageously lasts 3 to 10 hours.

At the end of the reaction, the desired product with formula (I) is obtained.

The product is recovered using conventional techniques employed in the field.

In particular, water hydrolysis can be carried out, preferably using ice employed in an amount of 100% to 150% by weight of the compound with formula (I) or (I'), for example.

A solid is obtained that is separated using conventional solid/liquid separation techniques, preferably by filtering.

The desired product is then produced.

In accordance with the process of the invention, the starting compound is a compound with formula (II) which can in particular be obtained using an O- or S-alkylation reaction of a compound of the 2-hydroxy or 2-thiobenzaldehyde type with formula (III) with a carboxylic acid or a derivative with formula (IV).

One implementation consists of reacting an aromatic compound with formula (III) with a carboxylic acid or a derivative with formula (IV): the reaction is carried out in the presence of a base, preferably in an organic solvent.

A further variation of the process of the invention consists of carrying out the O- or S-alkylation reaction in an aqueous medium in the presence of a base and a phase transfer catalyst.

Of the compounds with formula (III), salicylic aldehyde is preferred.

Regarding the carboxylic acid or derivative with formula (IV), esters of α-halogenocarboxylic acids are preferably used, more preferably methyl or ethyl 2-bromohexanoate.

The mole ratio between the compound with formula (III) and the compound with formula (IV) is advantageously between 1 and 1.2.

In accordance with the process of the invention, the 2-hydroxy or 2-thiobenzaldehyde type compound with formula (III) is reacted in its salt form with the carboxylic acid or derivative with formula (IV), in an organic solvent.

A salt form of a 2-hydroxy or 2-thiobenzaldehyde type compound that has been extemporaneously prepared can be used, but it is also possible to prepare it in situ by reacting the compound of the 2-hydroxy or 2-thiobenzaldehyde type compound and the base.

Thus a base, which can be mineral or organic, is used in the process of the invention.

Particularly suitable bases for use in carrying out the process of the invention are mineral bases such as alkali metal or alkaline-earth metal salts, preferably an alkali or alkaline-earth metal hydroxide, which may be sodium, potassium or calcium hydroxide; or an alkali metal carbonate or bicarbonate, preferably sodium carbonate.

It is also possible to use an organic base such as a quaternary ammonium hydroxide or an amine.

Preferred examples of quaternary ammonium hydroxides that can be used are tetraalkylammonium or trialkylbenzylammonium hydroxides in which the alkyl groups, which may be identical or different, represent a linear or branched alkyl chain containing 1 to 12 carbon atoms, preferably 1 to 6 carbon atoms.

Preferably, tetraethylammonium hydroxide, tetraethylammonium hydroxide or tetrabutylammonium hydroxide is used.

It is also possible to use trialkylbenzylammonium hydroxides, in particular trimethylbenzylammonium hydroxide.

Examples of amines that can be mentioned include tertiary amines.

Suitable bases that can be cited are tertiary amines, more particularly those with general formula (VIII):

$$N-(R_3)_3 \qquad (VIII)$$

in which:

groups $R_3$, which may be identical or different, represent hydrocarbon residues containing 1 to 20 carbon atoms, such as alkyl, cycloalkyl, aryl or heterocyclic groups;

2 groups $R_3$ together with the nitrogen atom form a heterocycle containing 4 to 6 atoms.

More particularly:

symbols $R_3$ represent an alkyl group containing 1 to 10 carbon atoms, preferably 1 to 4 carbon atoms, or a cyclopentyl or cyclohexyl group or pyridinyl group;

2 groups $R_3$ together form a piperidine or pyrrolidine cycle with the nitrogen atom.

Examples of such amines that can be cited are triethylamine, tri-n-propylamine, tri-n-butylamine, methyldibutylamine, methyldicyclohexylamine, ethyldiisopropylamine, N,N-diethylcyclohexylamine, dimethylamino-4-pyridine, N-methylpiperidine, N-methylpiperidine, N-ethylpiperidine, N-n-butylpiperidine, 1,2-dimethylpiperidine, N-methylpyrrolidine, and 1,2-dimethylpyrrolidine.

For reasons of economy, sodium or potassium carbonate are preferred.

While the base is used in its solid form, it is also possible to use the base in solution. The concentration of the starting base solution is not critical. The alkali metal hydroxide solution is employed in a concentration that is generally in the range 10% to 50% by weight The quantity of base introduced into the reaction medium takes into account the quantity necessary to change the hydroxyl or thiol function of the 2-hydroxy or 2-thiobenzaldehyde type compound into the salt form.

The hydroxyl or thiol group of the starting substrate with formula (III) can be transformed into its salt form in an initial step. Thus, the compound with formula (III) can be transformed into its salt form either by introducing the base then causing it to react at a temperature that is advantageously in the range 0° C. to 100° C., preferably in the range 25° C. to 50° C., or by introducing the base at the same time as the compound with formula (IV).

Generally, the quantity of base, expressed with respect to the 2-hydroxy or 2-thiobenzaldehyde type compound, is in the range 90% to 120% of the stoichiometric quantity.

In accordance with the invention, the O- or S-alkylation reaction is advantageously carried out in the liquid phase comprising the compound with formula (III) and the compound with formula (IV), in the presence of a base.

One of the starting reactants can act as the reaction solvent, but it is also possible to use an organic solvent.

An organic solvent is selected that is less activated than the starting substrate and which preferably dissolves it.

Examples of solvents that are suitable for use in the present invention that can be cited are aromatic hydrocarbons, which may or may not be halogenated, and aliphatic, cycloaliphatic or aromatic ether-oxides.

Examples of aliphatic hydrocarbons that can be cited are aromatic hydrocarbons, more particularly aromatic hydrocarbons such as benzene, toluene, xylenes, cumene, and petroleum cuts constituted by a mixture of alkylbenzenes, in particular Solvesso type cuts.

Regarding aliphatic or aromatic halogenated hydrocarbons, particular mention can be made of dichloromethane, 1,2-dichloroethane and mono- or dichlorobenzene.

The organic solvent can also be an aliphatic, cycloaliphatic or aromatic ether-oxide, more particularly dipropyl oxide, diisopropyl oxide, dibutyl oxide, methyltertiobutylether, ethylene glycol dimethylether (or glyme), diethylene glycol dimethyl ether (diglyme); phenyl oxide; dioxane, and tetrahydrofuran (THF).

Examples of more polar aprotic organic solvents that can also be used in the process of the invention that can be cited are aliphatic or aromatic nitriles such as acetonitrile, propionitrile, benzonitrile; linear or cyclic carboxamides such as N,N-dimethylacetamide (DMAC), dimethylformamide (DMF), diethylformamide or 1-methyl-2-pyrrolidinone (NM334P).

Preferred solvents are DMAC or DMF.

It is also possible to use a mixture of solvents.

Regarding the concentration of the 2-hydroxy or 2-thiobenzaldehyde type compound in the reaction medium, it is preferably in the range 2% to 50%. by weight.

In a variation of the process of the invention, iodide ions are added to accelerate the reaction. Alkali metal iodides can in particular be used, preferably potassium iodide or tetraalkylammonium iodides, preferably tetrabutylammonium iodide.

The quantity of iodide used, expressed as the ratio between the number of moles of iodine salt and the number of moles of compound with formula (III), can be in the range 0.05 to 0.2.

The temperature for reacting the aromatic compound with formula (III) with a carboxylic acid or derivative with formula (IV) is advantageously in the range 0° C. to 100° C., preferably in the range 25° C. to 50° C.

The reaction generally takes place at atmospheric pressure.

In a preferred variation of the process of the invention, the process of the invention is carried out in a controlled atmosphere of inert gases. A rare gas atmosphere can be established, preferably with argon, but it is cheaper to use nitrogen.

From a practical viewpoint, the process is simple to carry out.

One implementation of the invention consists of charging all of the reactants, the base, the organic solvent and optionally the iodide ions.

The medium is then heated to the selected reaction temperature.

As mentioned above, salt formation can be carried out in a previous step and the compound with formula (III), the base and the organic solvent can be introduced, the medium is heated to the selected temperature then the compound with formula (IV) is added along with the optional iodide ions, then heated.

The desired product with formula (II) is obtained.

The product obtained is recovered conventionally.

As an example, the salts formed during the reaction can be eliminated by adding water and extracting the product in the organic phase, in a suitable solvent, for example isopropyl ether.

The organic solvent can be eliminated conventionally by evaporation.

In a variation of the process of the invention, the 2-hydroxy- or 2-thiobenzaldehyde type compound with formula (III) is reacted with a carboxylic acid or derivative with formula (IV) in an aqueous medium in the presence of a base and a phase transfer catalyst.

The expression "phase transfer catalyst" means a catalyst that can pass the anion from the aqueous phase to the organic phase.

Known phase transfer catalysts can be used in the process of the invention, in particular those described by Jerry MARCH in "Advanced Organic Chemistry", third edition, John Wiley & Sons, 1985, p.320 ff.

A first category of phase transfer catalysts that is suitable for use in the invention includes those of the tris(ether-amine) type which have been described in the literature, in particular in French patent FR-A-2 455 570.

They have the following formula:

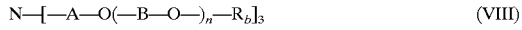

N—[—A—O(—B—O—)$_n$—R$_b$]$_3$             (VIII)

In which formula, R$_b$ represents an alkyl group containing 1 to 24 carbon atoms, a cyclohexyl group, a phenyl group, an alkylphenyl group the alkyl portion of which contains 1 to 12 carbon atoms, A and B, which may be identical or different, represent a linear alkanediyl group containing 2 or 3 carbon atoms, said atoms possibly being substituted by a methyl or ethyl group.

A specific example of catalysts with formula (VIII) that can in particular be mentioned is tris(3,3-dioxaheptyl)amine (TDA-1).

Catalysts that are preferably employed in the process of the invention are onium salts, more particular quaternary ammonium and/or phosphonium salts.

Onium salts that can be used in the process of the invention are those the onium ions of which derive in particular from nitrogen, phosphorus, arsenic, sulphur, selenium, oxygen, carbon or iodine and co-ordinated with hydrocarbon residues. Onium ions deriving from nitrogen, phosphorus or arsenic will be four-co-ordinate; onium ions deriving from sulphur, selenium, oxygen or carbon will be three-coordinated; while onium ions deriving from iodine will be two-coordinated.

The hydrocarbon residues co-ordinated to these different elements are alkyl, alkenyl, aryl, cycloalkyl, optionally substituted aralkyl groups, and two co-ordinated hydrocarbon residues can together form a single divalent group.

The nature of the anions bonded to these organic cations is not important. Any "hard" or "borderline" base will be suitable as the anion.

The terms "hard" or "borderline" base means any anion satisfying the conventional definition given by R. PEARSON in the Journal of Chem. Ed. 45, pages 581–587 (1968).

Particularly suitable onium ions that can be used in the process of the invention are those with the following general formulae:

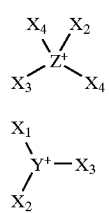

in which formulae:
  Z represents N, P or As;
  Y represents S, O, Se or C;
  $X_1$, $X_2$, $X_3$ and $X_4$, which may be identical or different, represent:
    a linear or branched alkyl group containing 1 to 16 carbon atoms, optionally substituted by one or more phenyl, hydroxyl, halogen, nitro, alkoxy or alkoxycarbonyl groups, the alkoxy groups containing 1 to 4 carbon atoms;
    a linear or branched alkenyl group containing 2 to 12 carbon atoms;
    an aryl group containing 6 to 10 carbon atoms, optionally substituted by one or more alkyl groups containing 1 to 4 carbon atoms, an alkoxy group, or an alkoxycarbonyl group, the alkoxy group containing 1 to 4 carbon atoms, or a halogen;
  two of said groups $X_1$ to $X_4$ can together form a linear or branched alkylene, alkenylene or alkadienylene group containing 3 to 6 carbon atoms.

The following ions included in "hard" or "borderline" bases that can constitute the anion in said onium salts can be cited: $F^-$, $ClO_4^-$, $PF_6^-$, $BF_4^-$, $SnCl_6^-$, $SbCl_6^-$, $B(Ph)_4^-$, $PO_4^{3-}$, $HPO_4^{2-}$, $H_2PO_4^-$, $CH_3SO_3^-$, $Ph-SO_3^-$, $HSO_4^-$, $NO_3^-$, $SO_4^{2-}$, $Cl^-$, $Br^-$, $I^-$, $OH^-$, Ph representing a phenyl group, and any other anion satisfying PEARSON's definition of a "hard" or "borderline" base.

For ease of implementation, said anions can be selected from $PO_4^{3-}$, $HPO_4^{2-}$, $H_3PO_4^-$, $CH_3SO_3^-$, $Ph-SO_3^-$, $NO_3^-$, $SO_4^{2-}$, $PF_6^-$, $Cl^-$, $Br^-$, $I^-$, $OH^-$, Ph having the meaning given above. Advantageously, $Br^-$ and $Cl^-$ anions are selected.

The following cations can be cited as examples of onium ions with formula (IX):

tributylmethylammonium;
tetraethylammonium;
tetrabutylammonium;
dodecyltrimethylammonium;
methyltrioctylammonium;
heptyltributylammonium;
tetrahexylammonium;
tetraheptylammonium;
tetraoctylammonium;
benzyltrimethylammonium;
benzyldimethylpropylammonium;
benzyldimethyloctylammonium;
benzyltributylammonium;
benzyltriethylammonium;
phenyltrimethylammonium;
benzyldimethyltetradecylammonium;
benzyldimethylhexadecylammonium;
tetrabutylphosphonium;
trimethylpentylphosphonium;
trimethylphenylphosphonium;
diethyldimethylphosphonium;
dicyclohexydimethylphosphonium;
dimethyldiphenylphosphonium;
cyclohexyltrimethylphosphonium;
methyltribenzylphosphonium;
methyltri(4methylphenyl)phosphonium;
ethyltri(n-propyl)phosphonium;
triethylpentylphosphonium;
hexadecyltributylphosphonium;
ethyltriphenylphosphonium;
n-butyltri(n-propyl)phosphonium;
tetraphenylphosphonium;
teiphenyl(4-meethylphenyl)phosphonium;
tetrakis(hydroxymethyl)phosphonium;
tetraphenylarsonium.

Examples of onium ions with formula (IX') that can be cited are the following cations:

triethylsulphonium;
triphenylsulphonium.

Preferred onium ions that can be used in the present process are quaternary ammonium ions and quaternary phosphonium ions.

Ammonium ions are particularly suitable, the ammonium ions including four alkyl groups containing 1 to 5 carbon atoms or a benzyl group.

Regarding the choice of anion, $Br^-$, $Cl^-$ or $OH^-$ are preferred.

The most suitable catalysts for use in the present invention are tributylbenzyl ammonium or phosphonium chloride or bromide, tetramethyl ammonium or phosphonium chloride or bromide, tetraethyl ammonium phosphonium chloride or bromide, and tetrabutyl ammonium or phosphonium chloride or bromide.

Benzyltributylammonium chloride or bromide is particularly preferred, the chlorinated derivative being more particularly preferred.

The onium salt can be introduced during the process of the invention in the solid state or in the form of a solution in one of its solvents, usually water.

The process of the invention is advantageously carried out in the absence of solvent.

The process of the invention is carried out in the presence of a water-soluble base.

Advantageously, potassium or sodium carbonate is used, or ammonia

In a preferred implementation, potassium carbonate is used.

The quantity of base employed, expressed as the ratio between the number of moles of compound with formula (III) an the number of moles of base, is preferably between 1 and 5, more preferably about 1.5.

In accordance with the process of the invention, the O- or S-alkylation reaction of the compound with formula (III) is carried out in the presence of a phase transfer catalyst, the different reactants generally being used in the proportions defined above.

The mole ratio between the number of moles of compound with formula (III) and the number of moles of compound with formula (IV) is preferably in the range 1 to 1.2.

Regarding the quantity of catalyst used, this is advantageously such that the mole ratio between said catalyst and the compound with formula (III) is in the range 0.01 to 0.50, preferably in the range 0.05 to 0.2. The upper limit is not critical and can be substantially exceeded without disadvantage as the catalyst can optionally be recycled at the end of the reaction.

As mentioned above, the reaction is carried out in an aqueous medium, advantageously in the absence of any organic solvent.

In a preferred implementation of the invention, the concentration of the compound with formula (III) is as high as possible.

The quantity of water present in the reaction medium generally represents 30% to 100% of the total weight of the reactants used.

The reaction is advantageously carried out following the "one pot" principle, and the order in which the reactants and reactive agents are introduced is not critical.

The temperature at which the process of the invention is carried out is generally in the range from ambient temperature to 80° C. Preferably, the temperature is in the range 50° C. to 65° C.

The reaction pressure is not critical and is generally atmospheric pressure.

In order to reach the temperatures indicated above, autogenous pressure conditions are usually applied.

The reaction period depends on the reaction temperature and on the desired degree of transformation. When the temperature is in the preferred zone, the reaction period can vary widely, for example, from 6 to 10 hours.

At the end of the reaction, the aromatic O- or S-alkylated compound with formula (II) is contained in or constitutes the organic phase, which can be separated from the aqueous phase, in particular by decanting.

The compound obtained can be isolated from the organic phase using conventional techniques such as distillation or extraction using a suitable solvent.

In accordance with the invention, the compound with formula (I) or (I') is an intermediate in the production of the compound with formula (V).

In a subsequent step, if necessary, the ester function can be saponified to the carboxylic function then the product obtained is cyclised. In a further variation, it is possible to carry out saponification of the compound with formula (II) if necessary, prior to the nitration operation.

To this end, the compound with formula (I) or (I') is reacted with a base in a hydro-organic medium.

A preferred base is sodium hydroxide or potassium hydroxide, used in the form of flakes or concentrated solutions, for example 40% for sodium hydroxide.

The quantity of base employed, expressed as the ratio between the number of moles of compound with formula (I) or (I') and the number of moles of base, is preferably between 1 and 5, more preferably between 1 and 2.

The base is dissolved in an aqueous or hydroorganic medium.

Preferably, a polar organic solvent is used.

More particular examples of suitable organic solvents that can be cited are aliphatic alcohols such as ethanol, propanol, butanol, pentanol, ethylene glycol; cycloaliphatic alcohols, in particular cyclohexanol, and arylaliphatic alcohols, more particularly benzyl alcohol. It is also possible to envisage the monomethyl, monoethyl, monopropyl, monobutyl ethers of ethylene glycol sold under the trade name Cellosolves®.

The concentration of compound with formula (I) or (I') in the reaction medium (water+organic solvents) advantageously varies between 5% and 50%, preferably in the range 5% to 20% by weight.

The volume ratio between the organic solvent and water can, for example, be between 0.1 and 0.9, preferably in the range 0.1 to 0.2.

The choice of organic solvent and the water/organic solvent ratio is determined so that the solution obtained is homogeneous.

The saponification reaction is carried out at a temperature in the range from ambient temperature to the reflux temperature of the reaction mixture, preferably at a temperature close to 50° C.

The term "ambient temperature" generally means a temperature in the range 15° C. to 25° C.

In one practical implementation of the invention, the compound with formula (I) or (I') is introduced into the aqueous or hydro-organic medium then the base is added, and the reaction mixture is heated to the selected temperature.

At the end of the reaction, if necessary, the excess base is neutralised with an acidic solution, preferably a solution of a mineral acid or a mineral salt such as hydrochloric acid or ammonium chloride.

The product obtained precipitates out then it is separated using conventional solid/liquid separation techniques, preferably by filtering.

The product obtained can be cyclised by applying prior art techniques, for example in acetic anhydride and in the presence of sodium acetate (Brady, W. T.; Gu, Y-Q., J. Heterocyl. Chem. 1988, 25, 969–971).

The temperature of the cyclisation reaction is advantageously between ambient temperature and the reflux temperature of the reaction solvent.

A benzofuran or benzothiophene type derivative that is nitrated in the 4 position is obtained with formula (V):

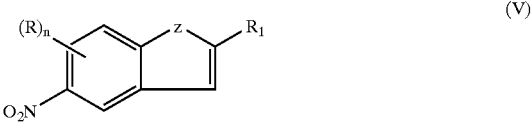

in which formula (V), R, $R_1$, Z and n have the meanings given above;

by optional saponification of the compound with formula (I) or (I') when $R_2$ is an ester function, then cyclising.

In a further implementation, the compound with formula (I) or (I') is cyclised in a medium comprising a carboxylic acid anhydride and the presence of a base selected from metallic or ammonium carbonates and/or bicarbonates.

Suitable bases that can be mentioned in particular are alkali or alkaline-earth metal carbonates and bicarbonates. Caesium carbonate can be used but preferably, sodium carbonate or potassium carbonate is used.

In accordance with the process of the invention, the aromatic compound, preferably with formula (I) or (I'), is cyclised in a carboxylic acid anhydride.

More particularly, this latter has the following formula:

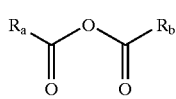
(X)

in which formula (X):

- $R_a$ and $R_b$, which may be identical or different, represent a monovalent hydrocarbon group that may or may not be substituted, which can be a linear or branched, saturated or unsaturated acyclic aliphatic group; or a monocyclic saturated, unsaturated or aromatic carbocyclic group;
- $R_a$ and $R_b$ can together form a divalent linear or branched, saturated or unsaturated aliphatic group containing at least 2 carbon atoms.

Groups $R_a$ and $R_b$ are preferably selected such that the anhydride is liquid under the reaction conditions.

The anhydride used may or may not be cyclic.

More precisely, a cyclic anhydride containing 5 to 10 carbon atoms in the cycle can be used that may or may not contain a double bond; one of the atoms can be replaced by an oxygen atom.

Preferably, the cyclic anhydrides are saturated or contain a double bond and 5 or 6 atoms in the cycle.

The cycle can comprise one or more substituents. More particular examples of substituents that can be cited are linear or branched alkyl groups containing 1 to 12 carbon atoms, preferably 1 to 4 carbon atoms, such as methyl, ethyl, propyl, isopropyl, butyl, isobutyl, sec-butyl, tert-butyl, or halogen atoms or a trihalogenomethyl group.

More particularly, when using a non cyclic anhydride with formula (X), groups $R_a$ and $R_b$, which may be identical or different, represent:

- a linear or branched acyclic aliphatic group preferably containing 1 to 24, more preferably 1 to 12 carbon atoms, which may be saturated or comprise one or more unsaturated bonds in its chain, generally 1 to 3 unsaturated bonds, which may be simple double bonds: the hydrocarbon chain may be interrupted by one of the following groups: —O—; —CO—; and/or carry one or more substituents, in particular: —X; —CX₃;
- a saturated, unsaturated or aromatic carbocyclic group containing 3 to 8 carbon atoms, preferably 6 carbon atoms, optionally carrying one or more halogen atoms, preferably chlorine or bromine.

Of the groups defined above, $R_a$ and $R_b$ preferably represent:

- a linear or branched alkyl group containing 1 to 12 carbon atoms, optionally carrying one or more halogen atoms;
- a cyclohexyl or phenyl group, optionally carrying one or more halogen atoms, or a trihalogenomethyl group.

Examples of anhydride that can be cited are:

acetic anhydride;
propanoic anhydride;
isobutyric anhydride;
trichloroacetic anhydride;
trifluoroacetic anhydride;
benzoic anhydride;
monochloroacetyl anhydride;
dichloroacetyl anhydride;
pivalic anhydride.

Acetic anhydride is preferred from the above list of anhydrides.

The invention does not exclude producing the carboxylic anhydride in the medium, from a carboxylic acid.

As mentioned above, in a preferred variation of the process of the invention, an organic solvent is used.

A number of criteria govern the choice of organic solvent.

A first criterion for the organic solvent is that it should be stable in the reaction medium.

A second criterion is that the solvent should have a high boiling point, preferably 50° C. or more.

Examples of solvents that are suitable for use in the present invention that can be cited are aromatic hydrocarbons, which may or may not be halogenated, and aliphatic, cycloaliphatic or aromatic ether-oxides. Examples of such solvents have been given above.

Examples of more polar aprotic organic solvents that can also be used in the process of the invention that can be cited are linear or cyclic carboxamides such as N,N-dimethylacetamide (DMAC), N,N-diethylacetamide, dimethylformamide (DMF), diethylformamide or 1-methyl-2-pyrrolidinone (NMP); dimethysulphoxide (DMSO); hexamethylphosphotriamide (HMPT); tetramethylurea; nitro compounds such as nitromethane, nitroethane, 1-nitropropane, 2-nitropropane or mixtures thereof, nitrobenzene; aliphatic or aromatic nitriles such as acetonitrile, propionitrile, butanenitrile, isobutanenitrile, benzonitrile, benzyl cyanide; tetramethylene sulphone (sulpholane).

It is also possible to use a mixture of organic solvents.

According to the process of the invention, the starting substrate is cyclised in the presence of a base and a carboxylic acid anhydride.

More precisely, the quantity of base, expressed as the ratio between the number of moles of base and the number of moles of starting substrate, preferably with formula (I) or (I'), is in the range 0.05 to 1.0 and is preferably in the range 0.1 to 0.2.

The quantity of carboxylic acid anhydride employed is such that the mole ratio of carboxylic acid anhydride/compound with formula (I) or (I') is preferably in the range 2 to 10.

In the preferred variation of the process of the invention, which consists of using an organic solvent, the quantity of carboxylic acid anhydride employed is such that the mole ratio of carboxylic acid anhydride/compound with formula (I) or (I')is preferably in the range 1 to 3, more preferably in the range 1 to 2.

Regarding the quantity of organic solvent employed, it is determined as a function of the nature of the organic solvent selected.

It is determined such that the concentration of substrate in the organic solvent is preferably in the range 1 to 10 mole/liter, more preferably in the range 2 to 3 mole/liter.

The starting substrate cyclising reaction takes place at a temperature that is advantageously in the range 50° C. to 160° C., preferably in the range 100° C. to 140° C.

The cyclisation reaction is generally carried out at atmospheric pressure but preferably, it is carried out in a controlled inert gas atmosphere. A rare gas atmosphere can be established, preferably with argon, but it is cheaper to use nitrogen.

From a practical viewpoint, the reaction is simple to carry out.

The order in which the reactants are used is not critical. A preferred variation consists of charging the organic solvent, if present, the substrate, the carboxylic anhydride and then the base and heating to the desired temperature.

At the end of the reaction, the cyclised product is obtained, preferably with formula (V) and which can be recovered conventionally.

More particularly, the invention concerns the preparation of 2-n-butyl-5-nitrobenzofuran.

The following examples illustrate the invention without in any way limiting its scope.

EXAMPLES

Example 1

Preparation of 2-(2-formyl-4-nitro-phenoxy)-hexanoic acid 2-(2-formyl-4-nitro-phenoxy)-hexanoic acid can be prepared as follows:

29.5 g of methyl 2-(2-formyl-4-nitro-phenoxy)-hexanoate and 148 ml of water were charged in succession into a 250 ml four-neck reactor provided with a Teflon half moon paddle stirrer, a thermometer, a 50 ml dropping funnel, a cooling coil and a nitrogen inlet.

8.4 g of an aqueous 50% sodium hydroxide solution was added over 20 minutes.

After stirring for 15 minutes at a temperature of close to 25° C., the reaction medium was heated for 2 hours to about 50° C.

The clear red medium obtained was partially evaporated (50 ml) under reduced pressure (20 mm Hg) to eliminate the methanol formed then rediluted with 50 ml of water.

The pH of the reaction medium was brought to about 1.8 by slowly adding 10.8 g of concentrated hydrochloric acid, keeping the temperature to close to 45° C. by stirring.

After stirring for one hour, the temperature of the medium was raised to close to 55° C. for 20 minutes then left at ambient temperature for 12 hours.

The solid product was separated by filtering through a n3 glass frit and washed with twice 50 ml of water and oven dried for 12 hours at a temperature of close to 55° C.

26.8 g of 2-(2-formyl-4-nitro-phenoxy)-hexanoic acid was obtained in the form of a pale yellow solid melting at 110–111° C. and titrating at 97.5% by potentiometric assay.

It had the following NMR spectrum:

$^1$H NMR (DMSO—d6): δ0.91 (t, 3H, $CH_3$); 1.38 (m, 2H, $C\underline{H}_2$—$CH_3$); 1.51 (m, 2H, $CH_2$—$CH_2$—$CH_3$); 2.02 (m, 2H, $C\underline{H}_2$—CH); 5.24 (t, 1H, CH); 7.34 (d, J=9 Hz, 1H, ArH); 8.44 (d, J=2 Hz, 1H, ArH); 8.47 (dd, J=9 Hz, J=2 Hz, 1H, ArH); 10.42 (s, 1H, CHO); 13.45 (broad peak, 1H, COOH).

Example 2

Preparation of 2-(2-formyl-4-phenoxy)-hexanoic acid 2-(2-formyl-4-phenoxy)-hexanoic acid can be prepared as follows:

29.5 g of methyl 2-(2-formyl-phenoxy)-hexanoate and 148 ml of water were charged in succession into a 250 ml four-neck reactor provided with a Teflon half moon paddle stirrer, a thermometer, a 50 ml dropping funnel, a cooling coil and a nitrogen inlet.

10.4 g of an aqueous 50% sodium hydroxide solution was added over 20 minutes.

After stirring for 15 minutes at a temperature of close to 25° C., the reaction medium was heated for 2 hours to about 50° C.

The clear medium obtained was partially evaporated (50 ml) under reduced pressure (20 mm Hg) to eliminate the methanol formed, then re-diluted with 50 ml of water.

The pH of the reaction medium was brought to about 1.8 by slowly adding 10.8 g of concentrated hydrochloric acid, keeping the temperature to close to 45° C. by stirring.

After stirring for one hour, the temperature of the medium was raised to close to 55° C. for 20 minutes then left at ambient temperature for 12 hours.

The solid product was separated by filtering through a n° 3 glass frit and washed with twice 50 ml of water then oven dried for 12 hours at a temperature of close to 55° C.

27.4 g of 2-(2-formyl-phenoxy)-hexanoic acid was obtained in the form of a pale yellow solid titrating at 98% by potentiometric assay.

EXAMPLE 3

Preparation of methyl 2-(2-formyl-4-nitro-phenoxy) hexanoate

Methyl 2-(2-formyl-4-nitro-phenoxy)-hexanoate can be prepared as follows:

123 g of 96% concentrated sulphuric acid was charged into a 250 ml four-neck reactor provided with a Teflon half moon paddle stirrer, a thermometer, a 50 ml dropping funnel, a cooling coil and a nitrogen inlet.

The reaction medium was cooled to a temperature of close to 5° C. then 30 g (0.12 mole) of methyl 2-(2-formylphenoxy)-hexanoate was added at the same temperature.

After stirring for 15 minutes, 15.9 g (0.126 mole) of nitrating mixture (50/50) was added over 2 hours, keeping the reaction medium close to 5° C., then 76.9 g of ice was added over 30 minutes, leading to an $H_2SO_4$ titre of 60%.

The reaction mixture was filtered through a n° 3 frit after stirring for 10 minutes.

The crude product obtained was dissolved in 100 ml of dichloromethane and washed with twice 50 ml of water.

The decanted organic phase was concentrated in a rotary evaporator at 20° C. to 70° C. in 20 mm of mercury (duration: 2 hours).

32.7 g of a beige yellow solid product was obtained, giving a yield of methyl 2-(2-formyl-4-nitro-phenoxy)-hexanoate of 92.4%, titrating at 96.7% by gas chromatography.

It had the following NMR spectrum:

$^1$H NMR (DMSO—d6): δ0.91 (t, 3H, $CH_3$); 1.38 (m, 2H, $C\underline{H}_2$—$CH_3$); 1.51 (m, 2H, $C\underline{H}_2$—$CH_2$—$CH_3$); 2.02 (m, 2H, $C\underline{H}_2$—CH); 5.24 (t, 1H, CH); 7.34 (d, J=9 Hz, 1H, ArH); 8.44 (d, J=2 Hz, 1H, ArH); 8.47 (dd, J=9 Hz, J=2 Hz, 1H, ArH); 10.42 (s, 1H, CHO); 13.45 (broad peak, 1H, COOH).

Example 4

Preparation of 2-(2-formyl-4-nitro-phenoxy)-hexanoic acid 2-(2-formyl-4-nitro-phenoxy)-hexanoic acid can be prepared as follows:

123 g of 96% concentrated sulphuric acid was charged into a 250 ml four-neck reactor provided with a Teflon half moon paddle stirrer, a thermometer, a 50 ml dropping funnel, a cooling coil and a nitrogen inlet.

The reaction medium was cooled to a temperature of close to 5° C. then 28.4 g (0.12 mole) of 2-(2-formylphenoxy)-hexanoic acid was added at the same temperature.

After stirring for 15 minutes, 15.9 g (0.126 mole) of nitrating mixture (50/50) was added over 2 hours, keeping the reaction medium close to 5° C., then 76.9 g of ice was added over 30 minutes, leading to an $H_2SO_4$ titre of 60%.

The reaction mixture was filtered through a n°3 frit.

The solid obtained was dissolved in 100 ml of dichloromethane and washed with twice 50 ml of water.

The decanted organic phase was concentrated in a rotary evaporator at 20° C. to 70° C. in 20 mm of mercury (duration: 2 hours).

32.1 g of a beige yellow solid product was obtained, giving a yield of methyl 2-(2-formyl-4-nitro-phenoxy)-hexanoate of 95%, titrating at 97.0% by gas chromatography.

It had the following NMR spectrum:

$^1$H NMR (DMSO—d6): δ0.91 (t, 3H, $CH_3$); 1.38 (m, 2H, $C\underline{H}_2$—$CH_3$); 1.51 (m, 2H, $C\underline{H}_2$—$CH_2$—$CH_3$); 2.02 (m, 2H, $C\underline{H}_2$—CH); 5.24 (t, 1H, CH); 7.34 (d, J=9Hz, 1H, ArH); 8.44 (d, J=2 Hz, 1H, ArH); 8.47 (dd, J=9 Hz, J=2 Hz, 1H, ArH); 10.42 (s, 1H, CHO); 13.45 (broad peak, 1H, COOH).

Example 5

Preparation of methyl 2-(2-formylphenoxy)-hexanoate

Methyl 2-(2-formylphenoxy)-hexanoate can be prepared as follows:

87.1 g (0.714 mole) of salicylic aldehyde, 158.2 g (0.756 mole) of methyl 2-bromohexanoate, 103.5 g (0.75 mole) of potassium carbonate and 5.9 g (0.0355 mole) of potassium iodide were charged in succession into a 1 liter four-neck flask provided with a half moon paddle stirrer, a thermometer, a cooling coil and a 500 ml dropping funnel.

400 g of dimethylformamide was added and the mixture was heated with stirring at a temperature of close to 80° C. for 4 hours.

After cooling to a temperature of close to 25° C., the reaction mixture was filtered through a n°3 glass frit and washed with 50 g of dimethylformamide.

The filtrate was concentrated by evaporation under reduced pressure (25–40 mbars) then diluted with 100 ml of water and successively extracted with a 100 ml batch of dichloromethane then 50 ml of dichloromethane.

The combined organic phases were washed with 50 ml of water and concentrated to dryness by evaporation under reduced pressure.

176.1 g of a clear yellow liquid was obtained, corresponding to a yield of 98.6% of methyl 2-[2-(formylphenoxy)]-hexanoate, titrating at 99.6% pure using gas chromatography.

Example 6

Preparation of methyl 2-(2-formylphenoxy)-hexanoate

Methyl 2-(2-formylphenoxy)hexanoate can be prepared as follows:

130.6 g (1.071 mole) of salicylic aldehyde, 237.3 g (1.134 mole) of methyl 2-bromohexanoate and 155.2 g (1.125 mole) of potassium carbonate were charged in succession into a 2 liter four-neck flask provided with a half moon paddle stirrer, a thermometer, a cooling coil and a 1000 ml dropping funnel.

600 g of dimethylformamide was added and the mixture was heated with stirring to a temperature of close to 80° C. for 4 hours.

After cooling to a temperature of close to 25° C., the reaction mixture was filtered through a n°3 glass frit and washed with 75 g of dimethylformamide.

The filtrate was concentrated by evaporation under reduced pressure (25–40 mbars) then diluted with 150 ml of water and successively extracted with a 150 ml batch of dichloromethane then 75 ml of dichloromethane.

The combined organic phases were washed with 75 ml of water and concentrated to dryness by evaporation under reduced pressure.

265 g of a clear yellow liquid was obtained, corresponding to a yield of 98.9% of methyl 2-[2-(formylphenoxy)]-hexanoate, titrating at 99.6% pure using gas chromatography.

What is claimed is:

1. A process for preparing nitroaromatic compounds with formula(I):

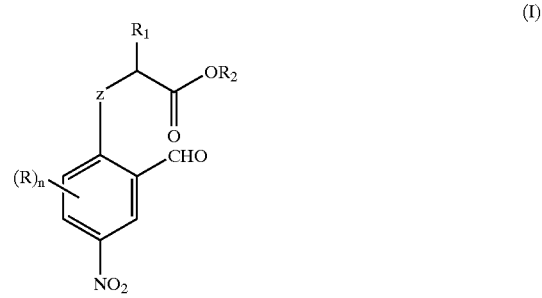

wherein:

$R_1$ represents a linear or branched alkyl group containing 1 to 12 carbon atoms, a phenyl group optionally substituted by an allyl group containing 1 to 4 carbon atoms, or a halogenophenyl group;

$R_2$ represents a hydrogen atom, or a hydrocarbon group containing 1 to 12 carbon atoms, being a linear or branched alkyl group, a cycloalkyl group, a phenyl group or a phenylalkyl group;

Z represents an oxygen or sulfur atom;

R represents a hydrogen atom or a group selected form the group consisting of:

a hydroxyl group;

a linear group containing 1 to 6 carbon atoms;

an alkoxy group containing 1 to 6 carbon atoms;

an ester group containing 1 to 10 carbon atoms;

an alkylamide group containing 1 to 6 carbon atoms;

a carboxamide group;

a halogen atom; and a trifluoromethyl group; and n is a number equal to 1, 2 or 3;

said process comprising the step of carrying out a selective nitration in position 4 of a stating aromatic compound, using a source of $NO2^+$, in the presence of sulfuric acid, the starting aromatic compound having the following formula (II):

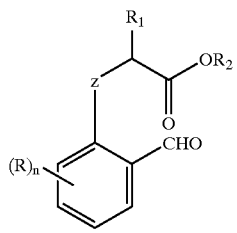

(II)

wherein R, $R_1$, $R_2$, Z and n have the meanings given above.

2. The process according to claim 1, wherein R represents a methyl, ethyl, propyl, isopropyl, butyl, isobutyl, sec-butyl, or tert-butyl group.

3. The process according to claim 1, wherein R represents a methoxy or ethoxy group.

4. The process according to claim 1, wherein $R_1$ represents an alkyl group containing 1 to 4 carbon atoms.

5. The process according to claim 1, wherein $R_2$ represents an alkyl group containing 1 to 4 carbon atoms.

6. The process according to claim 1, wherein Z is an oxygen atom.

7. The process according to claim 1, wherein the nitration is carried out in the presence or absence of an organic solvent.

8. The process according to claim 7, wherein the nitration is carried out in the presence an organic solvent, said organic solvent being an aliphatic halogenated hydrocarbon.

9. The process according to claim 8, wherein the organic solvent is dichloromethane.

10. The process according to claim 7, wherein the source of $NO_2^+$ is nitrogen dioxide $NO_2$, nitrous anhydride $N_2O_3$, dinitrogen tetroxide $N_2O_4$, a nitric oxide NO associated with an oxidising agent being nitric acid, nitrogen dioxide or oxygen, nitrous acid, nitrosyl sulphate or a nitrous salt.

11. The process according to claim 10, wherein the nitrous salt is sodium nitrite or an alkyl nitrite.

12. The process according to claim 7, wherein a nitrating mixture comprising nitric acid, as a source of $NO_2^+$, and sulfuric acid is used.

13. The process according to claim 7, wherein the source of $NO_2^+$ is nitric acid, the quantity of nitric acid, expressed as the mole ratio between the aromatic starting aromatic compound and nitric acid, is of from 0.9 to 1.1.

14. The process according to claim 13, wherein the quantity of nitric acid is of from 0.95 to 1.05.

15. The process according to claim 7, wherein the quantity of sulfuric acid, expressed as the mole ratio between the starting aromatic compound and the sulfuric acid is of from 0.9 to 1.1.

16. The process according to claim 15, wherein the quantity of the sulfuric acid is of from 0.95 to 1.05.

17. The process according to claim 7, wherein the nitration is carried out at a temperature of from −10° C. to 20° C.

18. The process according to claim 17, wherein the temperature is of from −5° C. to 10° C.

19. A nitroaromatic compound with the following formula (I'):

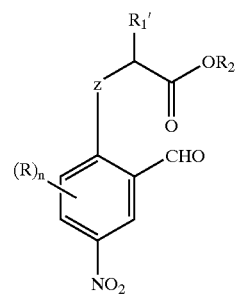

(I')

wherein

R represents a hydrogen atom or a group selected form the group consisting of the following group;

a hydroxyl group;

a linear or branched alkyl group containing 1 to 6 carbon atoms;

an alkoxy group containing 1 to 6 carbon atoms;

an ester group containing 1 to 10 carbon atoms;

an alkylamide group containing 1 to 6 carbon atoms;

a carboxamide group;

a halogen atom; and a trifluoromethyl group $R'_1$ represents a linear or branched alkyl group containing 1 to 12 carbon atoms, a phenyl group optionally substituted by an alkyl group containing 1 to 4 carbon atoms, or a halogenophenyl group;

$R_2$ represents a hydrogen atom, or a hydrocarbon group containing 1 to 12 carbon atoms, being a linear or branched alkyl group, a cycloalkyl group, a phenyl group or a phenylalkyl group;

Z represents an oxygen or sulphur atom;

R represents a hydrogen atom or a substituent; and n is a number equal to 1, 2 or 3.

20. The nitroaromatic compound according to claim 19, wherein R represents a hydrogen atom, a methyl group, an ethyl group, a methoxy group or an ethoxy group.

21. The nitroaromatic compound according to claim 19, wherein $R'_1$, represents an alkyl group containing 1 to 4 carbon atoms.

22. The nitroaromatic compound according to claim 19, wherein $R_2$ represents an alkyl group containing 1 to 4 carbon atoms.

23. The nitroaromatic compound according to claim 21, wherein $R_2$ represents an alkyl group containing 1 to 4 carbon atoms, n=1, and R is a hydrogen atom.

24. The nitroaromatic compound according to claim 23, being:

2-(2-formyl-4-nitro-phenoxy)-hexanoic acid, or methyl 2-(2-formyl-4-nitro-phenoxy)-hexanoate.

* * * * *